United States Patent [19]

Scott

[11] Patent Number: 5,341,436
[45] Date of Patent: Aug. 23, 1994

[54] NONDESTRUCTIVE ANALYSIS OF DISPERSION AND LOADING OF REINFORCING MATERIAL IN A COMPOSITE MATERIAL

[75] Inventor: David M. Scott, Wilmington, Del.

[73] Assignee: E. I. du Pont de Nemours and Company, Wilmington, Del.

[21] Appl. No.: 973,196

[22] Filed: Nov. 6, 1992

Related U.S. Application Data

[63] Continuation of Ser. No. 606,799, Oct. 31, 1990, abandoned.

[51] Int. Cl.$^5$ .............................................. G06K 9/00
[52] U.S. Cl. ........................................ 382/1; 364/507
[58] Field of Search ................... 382/1, 8, 18; 378/53, 378/54, 58, 61–63; 250/358.1, 390.04, 391; 364/473, 507; 73/159, 160, 866

[56] References Cited

U.S. PATENT DOCUMENTS

| | | | |
|---|---|---|---|
| 4,535,246 | 8/1985 | Shani | 250/358.1 |
| 4,575,634 | 3/1986 | Redler et al. | 250/358.1 |
| 4,668,867 | 5/1987 | Lingenfelter | 250/358.1 |
| 4,897,796 | 1/1990 | Salvado | 364/497 |

FOREIGN PATENT DOCUMENTS

| | | |
|---|---|---|
| 3533913 | 4/1987 | Fed. Rep. of Germany. |
| 63-67551 | 3/1988 | Japan. |
| 2179230 | 2/1987 | United Kingdom. |

OTHER PUBLICATIONS

Afshari et al., "QC Analysis of Glass and Filler Levels," Plastics Compounding (May/Jun. 1989), pp. 31–35.

Antrim, R. F., "Determination of Fiber Content in Long Fiber Reinforced Composites by Scanning Electron Microscopy and Image Analysis", Scanning Microscopy, vol. 2, No. 4 (1988), pp. 2001–2006.

Boulay et al., "Analysis of Filler Concentration and Orientation in Reinforced Polymers by Far-Ir Techniques", SPIE, vol. 665, Optical Techniques for Industrial Inspection, (1986), pp. 352–360.

Duke, J. C., "Nondestructive Characterization of Chopped Glass Fiber Reinforced Composite Materials", Short Fiber–Reinforced Composite Materials, ed. B. A. Sanders, ASTM STP 772, (1982), pp. 97–112.

Entine, G. et al., "The Application of Radiation Sensors to Reinforced Composite Analysis", Sensors EXPO Proceedings, (1987), pp. 153–157.

Forsell, B., "Microwaves for Measuring the Glass-Fibre Content", Fourth European Microwave Conference, (Microwave Exhibitions & Publishers, Surrey, England, 1974).

Galich, V. A., "Nondestructive Contactless Ultrasound Testing of the Binder Content of an Impregnated Reinforcing Material", Mekh. Kompoz Mater., (Zinatne), 3:554–556 (1989).

(List continued on next page.)

Primary Examiner—Joseph Mancuso
Assistant Examiner—Steven P. Klocinski

[57] ABSTRACT

A real-time radioscopy system produces an X-ray image of a sample of reinforced composite material or a manufactured part that has been molded from the reinforced composite material. By examining the statistics of the distribution of gray levels within the image, it is possible to measure the local and average reinforcing material content (loading) as well as how well the reinforcing material is distributed (the reinforcing material dispersion). The mean gray level is used to determine the local loading of the reinforcing material, which is measured as a function of position in the sample or part using this technique. In addition, an average value of the loading may be obtained. The standard deviation of the gray level image correlates with the quality of dispersion of the reinforcing material.

10 Claims, 8 Drawing Sheets

OTHER PUBLICATIONS

Galich, V. A., et al., "Effect of the Structure of Hybrid Composites Containing Carbon Fibers on the Results of Eddy-Current Testing", Mekh. Kompoz. Mater., (Zinatne), 4:707–710 (1986).

Hofer, V. G., et al., "Nondestructive Determination of Glass Content and of Voids in Reinforced Plastics", *Material Prof*, vol. 17, No. 1, (Jan. 1975), pp. 17–19.

Martin, B. G., "Analysis of Radiographic Techniques for Measuring Resin Content in Graphite Fiber-Reinforced Epoxy Resin Composites", *Materials Evaluation*, (Sep., 1977), pp. 65–75.

Monks, R., "Automatic Pellet Quality Inspection by Video Camera", *Plastics Technology*, (Jun. 1990), p. 45.

Owston, C. N., "Eddy Current Methods for the Examination of Carbon Fibre Reinforced Epoxy Resins", *Materials Evaluation*, (Nov. 1976), pp. 237–244.

Packer, T. W. et al., "Nondestructive Inspection of Glass-Reinforced Plastics", *British Journal of NDT*, (May 1980), pp. 135–138.

Scott, D. M., "Density Measurements from Radioscopic Images", *Materials Evaluation*, vol. 47, (Oct. 1989), pp. 1113–1119.

Yomoda et al., "The Measurement of Fiber Volume Content in Flex by Ultrasonic Wave Method", Industrial Products Research Institute, Tokyo, (May 1974), pp. 1080–1085.

Reynolds, W. N., "Ultrasonic Wave Velocities in Carbon-Fibre Reinforced Plastics".

| 69 | 69 | 69 | 66 |
|----|----|----|----|
| 69 | 72 | 69 | 66 |
| 69 | 69 | 69 | 66 |
| 66 | 66 | 66 | 63 |

FIG.5b

| .371 | .371 | .371 | .415 |
|------|------|------|------|
| .371 | .327 | .371 | .415 |
| .371 | .371 | .371 | .415 |
| .415 | .415 | .415 | .459 |

FIG.5c

| .10 | .10 | .10 | .15 |
|-----|-----|-----|-----|
| .10 | .05 | .10 | .15 |
| .10 | .10 | .10 | .15 |
| .15 | .15 | .15 | .20 |

FIG.5d

| .90 | .90 | .90 | .85 |
|-----|-----|-----|-----|
| .90 | .95 | .90 | .85 |
| .90 | .90 | .90 | .85 |
| .85 | .85 | .85 | .80 |

LOT 2A

LOT 2B

LOT 2C

LOT 2D

LOT 2E

LOT 2F

LOT 2G

STANDARD DEVIATION OF GREY LEVEL VALUES

FIG.8

NONDESTRUCTIVE ANALYSIS OF DISPERSION AND LOADING OF REINFORCING MATERIAL IN A COMPOSITE MATERIAL

This is a continuation of application Ser. No. 07/606,799 filed Oct. 31, 1990, now abandoned.

BACKGROUND OF THE INVENTION

1. Field of the Invention

The present invention relates to the field of analysis of composite material, and more specifically to the nondestructive analysis of the loading and dispersion of reinforcing material in a composite material.

2. Description of the Related Art

Composite materials are an important segment of the structural materials market. The high specific strength and specific stiffness characteristics of some composite systems make composite materials particularly valuable. However, due to the inherent nature of composite materials, their properties are extremely sensitive to the materials' microstructure. A composite material may be characterized as a multiphase structure combining one or more reinforcing materials in a matrix. Variations in distribution, orientation, or amount of reinforcing material or matrix content from point to point in a sample of the composite material can give rise to large differences in material properties. In addition, the composite material used in the manufacture of parts is in many cases fabricated at the time of manufacture. Any material defects are thus incorporated in the final manufactured part, allowing no chance for elimination of these defects prior to manufacture.

To control the quality of the composite material, it is necessary to control the level of loading of the reinforcing material. It is also especially important to control the quality of dispersion of the reinforcing material, since dispersion affects material properties as well as appearance. Nondestructive evaluation techniques offer a potential means of identifying such properties without destroying the sample or the part of composite material.

Generally, destructive techniques are used to determine percent loading. The most common method is to weigh and ash the samples. This process takes as long as 40 minutes per sample and is not suitable, for example, for glass-reinforced fluoropolymers because the matrix of fluoropolymers reacts with the glass at the elevated temperatures associated with ashing. Ultrasonic (non-imaging) equipment is available commercially and can perform nondestructive analysis for generating a low-resolution map showing variations in matrix content across the surface of a sample. However, this equipment does single point measurement and is extremely slow. Also, it is necessary to calibrate this equipment with a set of known calibration samples, which is time-consuming.

Dispersion is ordinarily determined qualitatively. Nondestructive techniques for determining dispersion qualitatively include ultrasonic or film-based radiographic imaging. With ultrasonic imaging techniques, interpretation of the images is at best a slow and highly subjective procedure. Radiographic imaging using silver-based photographic film requires development of the film and then interpretation of the image, which is also subjective. Nevertheless, it can uncover gross defects, such as agglomerations and stress risers.

Dispersion may also be determined quantitatively. For instance, dispersion may be determined by multiple sampling and ashing of small sections of samples. However, this is a tedious and time-consuming procedure. Also, computed tomography may be used to determine fiber dispersion characteristics, as disclosed in Japanese Patent Application Publication Kokai 63-67551. This Publication discloses a method of evaluating the fiber dispersion characteristics in a fiber-reinforced composite material based on the histograms of cross-sectional images produced by X-ray transmission computed tomography. However, this approach uses reconstructive imaging techniques to produce a final image; consequently, it is expensive and is not able to give instantaneous feedback.

It is therefore an object of the present invention to provide a nearly instantaneous, quantitative, nondestructive method which does not rely on reconstructive imaging techniques for analyzing the loading and/or the dispersion of reinforcing material in a sample of composite material and an apparatus for performing this method.

It is also an object of the present invention to provide such a method and apparatus for analyzing the dispersion and/or the loading of reinforcing material in a composite material from which a final part has been manufactured.

It is further an object of the present invention to provide a method and an apparatus which can simultaneously analyze both dispersion and loading of reinforcing material in a sample of composite material.

Still another object of the present invention is to provide an apparatus and a method for producing and digitizing a film-based radiographic image of a sample of composite material to analyze the dispersion and/or loading of the reinforcing material in the sample.

Yet another object of the present invention is to provide a method for mapping the variation in the amount of reinforcing material in a composite material using either a radioscopic or a radiographic image of a sample of the composite material.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

SUMMARY OF THE INVENTION

To achieve the foregoing objects, and in accordance with the purposes of the invention as embodied and broadly described herein, in accordance with the first embodiment of the present invention there is provided an apparatus for determining at least one of the loading and the dispersion of reinforcing material in a composite material, comprising: means for producing a through-transmission projection image of a sample of the composite material; means for producing a digitized electronic image from the through-transmission projection image; and computer means for analyzing the projection image to determine at least one of the dispersion and the loading of the reinforcing material in the sample.

Further in accordance with the first embodiment of the present invention there is provided a method of determining at least one of the dispersion and the loading of reinforcing material in a composite material, comprising the steps of: producing a visible, radioscopic image of a sample of the composite material; recording the radioscopic image of the sample; generating an image signal from the radioscopic image; producing a digitized electronic image from the image signal; and analyzing the digitized electronic image to determine at least one of the dispersion and the loading of the reinforcing material in the sample.

Further in accordance with the first embodiment of the present invention there is provided an apparatus for determining at least one of the dispersion and the loading of reinforcing material in a composite material, comprising: means for producing a visible, radioscopic image of a sample of the composite material; image recording means for recording the radioscopic image of the sample and for generating an image signal from the radioscopic image; buffer means for receiving the image signal and for producing a digitized electronic image from the image signal; and computer means for analyzing the digitized electronic image to determine at least one of the dispersion and the loading of the reinforcing material in the sample.

According to a second embodiment of the present invention, the apparatus further includes an image processor connected to the image recording means, wherein the image signal has gains and offsets and the image processor renormalizes the gains and offsets of the image signal.

According to a third embodiment of the present invention it is preferable that the apparatus includes an X-Y table for holding the sample and driving means for moving the X-Y table, wherein the computer means controls the driving means.

In accordance with a fourth embodiment of the present invention, there is further provided a method for determining at least one of the dispersion and the loading of reinforcing material in a composite material, comprising the steps of: producing a film-based radiographic image of a sample of the composite material; producing a digitized electronic image from the radiographic image; and analyzing the digitized electronic image to determine at least one of the dispersion and the loading of the reinforcing material in the sample.

In accordance with the fourth embodiment of the present invention, there is further provided an apparatus for determining at least one of the dispersion and the loading of reinforcing material in a composite material, comprising: means for producing a film-based radiographic image of a sample of the composite material; means for producing a digitized electronic image from the radiographic image; and computer means for analyzing the digitized electronic image to determine at least one of the dispersion and the loading of the reinforcing material in the sample.

All the embodiments of the present invention further include a method of mapping the variation in the amount of reinforcing material in a composite material, comprising the steps of: producing a through-transmission projection image of a sample of the composite material; generating an image signal from the through-transmission image; producing a digitized electronic image of the image signal; renormalizing the gains and offsets in the digitized electronic image; determining the local gray level values of the renormalized, digitized electronic image at a predetermined resolution, calculating the local attenuation coefficients of the sample from each of the gray level values; and determining the local loading values from each of the local attenuation coefficients.

BRIEF DESCRIPTION OF THE DRAWINGS

The accompanying drawings, which are incorporated in and constitute a part of the specification, illustrate the presently preferred embodiments of the invention and, together with the general description given above and the detailed description of the preferred embodiments given below, serve to explain the principles of the invention.

DETAILED DESCRIPTION OF THE DRAWINGS

Reference will now be made in detail to the present preferred embodiments of the invention as illustrated in the accompanying drawings.

Figure 1:
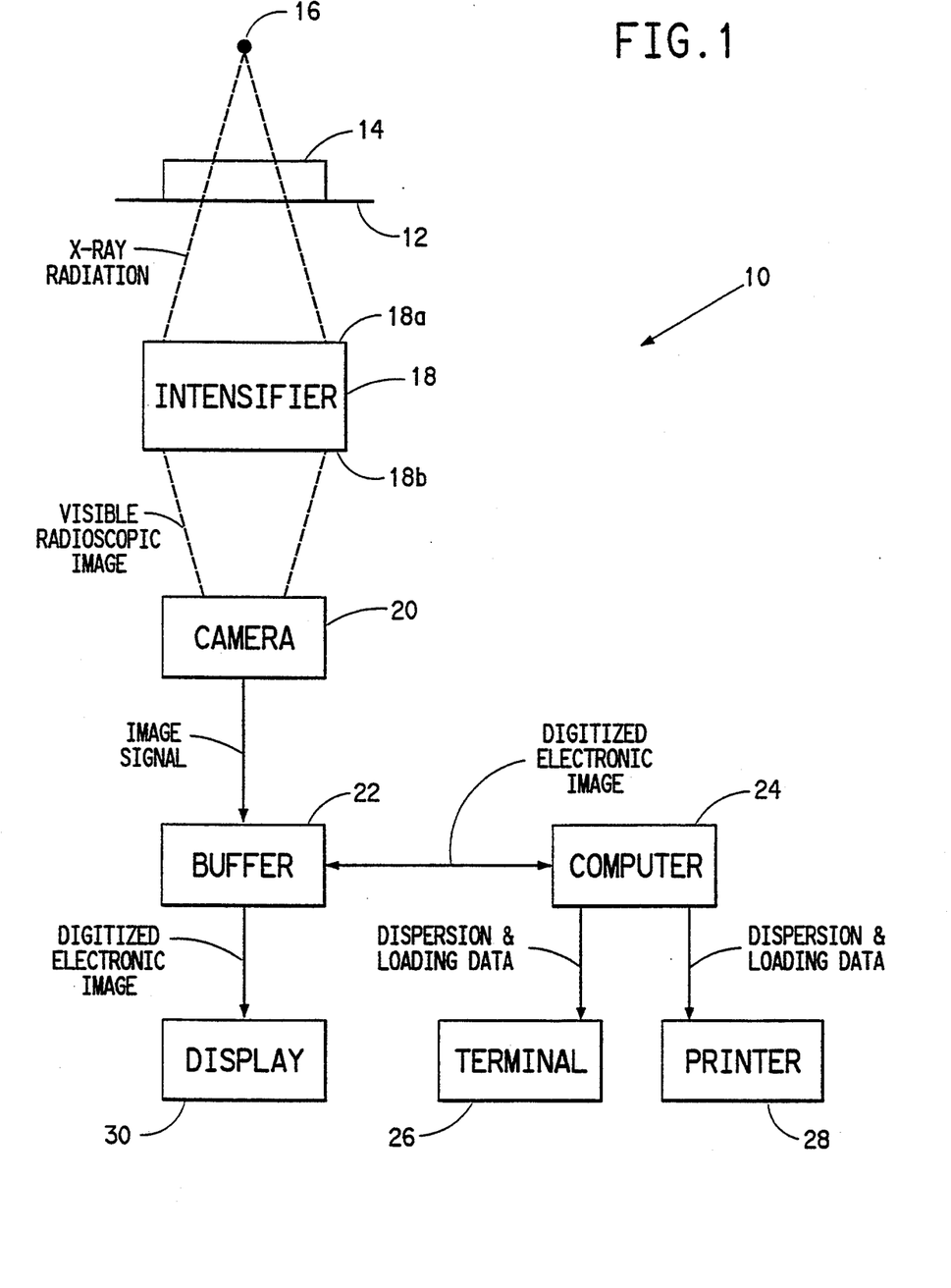
FIG. 1 is a schematic view of a first embodiment of the apparatus of the present invention.

In accordance with the present invention there is provided an apparatus for determining at least one of the dispersion and the loading of reinforcing material in a matrix of composite material. Referring to FIG. 1, the apparatus chosen for purposes of illustration is denoted generally at 10. The apparatus includes means for producing a through-transmission projection image of a sample of the composite material. The through-transmission projection image produced in the first, second and third embodiments is a radioscopic image, i.e., a real-time X-ray transmission projection image of the sample. In this context, radioscopy refers to producing a two-dimensional projection X-ray image of a three-dimensional object in real time, which affords simultaneous data collection. The through-transmission projection image produced in the fourth embodiment is a radiograph, i.e., a film-based X-ray transmission projection image of the sample.

The means for producing a through-transmission projection image comprises sample holder means for holding a sample of the composite material. The sample holder means comprises a sample holder 12 for holding a sample 14 of the composite material as shown in FIG. 1. The sample comprises a test bar. Alternatively, the sample comprises a manufactured part, such as a drill housing, which is made of composite material. Holder 12 is a frame which is relatively transparent to X-rays at a predetermined wavelength. The predetermined wavelength is dependent on the type of composite material and the reinforcing material sampled.

As embodied herein, the means for producing a through-transmission projection image of a sample of the composite material further comprises an X-ray source. As shown in FIG. 1, an X-ray source 16 is mounted in alignment with sample 14. X-ray source 16 is preferably a micro-focus unit, such as model KM10005S, which is commercially available from Kevex in Scotts Valley, Calif. X-ray source 16 passes X-ray radiation through sample 14 to produce a latent X-ray image of the sample. "Latent" in this context means invisible.

In accordance with the invention, the means for producing a through-transmission projection image of a sample further includes image intensifier means. The X-ray transmission means may include an image intensifier 18 as shown in FIG. 1, or may include a fluorescent screen and a low light-level camera. As shown in FIG. 1, image intensifier 18 is mounted in alignment with sample 14. Although image intensifier 18 and X-ray source 16 are shown in FIG. 1 in vertical alignment with the sample, the image intensifer, the X-ray source and the sample may be arranged in any configuration, so long as X-ray radiation from the source can pass through the sample and to the intensifier. Image intensifier 18 includes an input screen 18a and output screen 18b, wherein the radiation from X-ray source 16 passing through sample 14 impinges on input screen 18a and output screen 18b displays a visible, radioscopic image of sample 14. The image intensifier used in the present invention is a commercially available, off-the-shelf item. An example of an image intensifier suitable for use with the present invention is model S41026, which is commercially available from Machlett Laboratories in Stamford, Conn.

The sample holder means, the X-ray source and the image intensifier means comprise means for producing a visible, radioscopic image of a sample of the composite material.

As embodied herein, the means for producing a through-transmission projection image of the present invention further comprises image recording means for recording the radioscopic image of the sample and generating an image signal of the radioscopic image. Preferably, the image recording means comprises real-time recording means, such as a video camera 20 as shown in FIG. 1. Although video camera 20 is shown in FIG. 1 in vertical alignment with image intensifier 18, it may be arranged in any configuration with respect to the image intensifier, so long as it is mounted on the same optical axis as the image intensifier. The video camera is preferably a charge-coupled device (CCD) camera, such as model 4815, which is commercially available from Cohu, Inc. in San Diego, Calif.

In accordance with the invention, the present invention includes buffer means for receiving the image signal and for producing a digitized electronic image from the image signal. Preferably, the buffer means is a video frame buffer 22 as shown in FIG. 1. Buffer 22 receives the image signal generated by video camera 20 and produces a digitized electronic image from this image signal.

The present invention includes computer means for analyzing the digitized electronic image to determine the loading and the dispersion of the reinforcing material in the sample. The computer means is a microcomputer 24 which uses applicant's proprietary computer program to analyze the loading and the dispersion of the reinforcing material in sample 14. Microcomputer 24 includes a terminal 26 for interface with the operator and printer 28 for printing out the results of the analysis.

As the latent image is transformed to the radioscopic image, the radioscopic image to the image signal and the image signal to the digitized electronic image, intensifier 18, camera 20 and buffer 22 produce gains and offsets. The computer means of the present invention also renormalizes the gains and offsets in the digitized electronic image. In general, the intensity f(I) at a point in the digitized electronic image is related to the intensity I at the corresponding point on input screen 18a of intensifier 18 by the equation $f(I) = aI + b$, where a is the gain and b is the offset. The gain and offset are a function of position in the image space (x,y). To correct these gains and offsets, the radioscopic image r(x,y) must be renormalized, where r is an array, each element of the array is a pixel, and the numerical value associated with the brightness of each pixel is the gray level at that pixel. The radioscopic image r(x,y) is renormalized by calculating $R = (\text{scale factor}) * (r-b)/a$, where R(x,y) is the corrected (renormalized) image and r, R, a and b are functions of position (x,y). The values a(x,y) and b(x,y) are determined empirically: the offset b(x,y) (the black level) is the digitized electronic image with the X-ray source turned off, and the gain a(x,y) (the white level) is the digitized electronic image with the X-ray source on and with no sample in the X-ray beam. The values of a(x,y) and b(x,y) do not change unless the source conditions are changed, or they change very slowly due to drift in the electronic circuits of camera 20. The renormalization may be carried out as part of the computer program of microcomputer 24.

As embodied herein, the present invention further includes image display means for displaying the digitized electronic image. Preferably, the image display means comprises a TV display 30 which displays the digitized electronic image produced by buffer 22. TV display 30 is optional and is used for diagnostic purposes.

Figure 2:
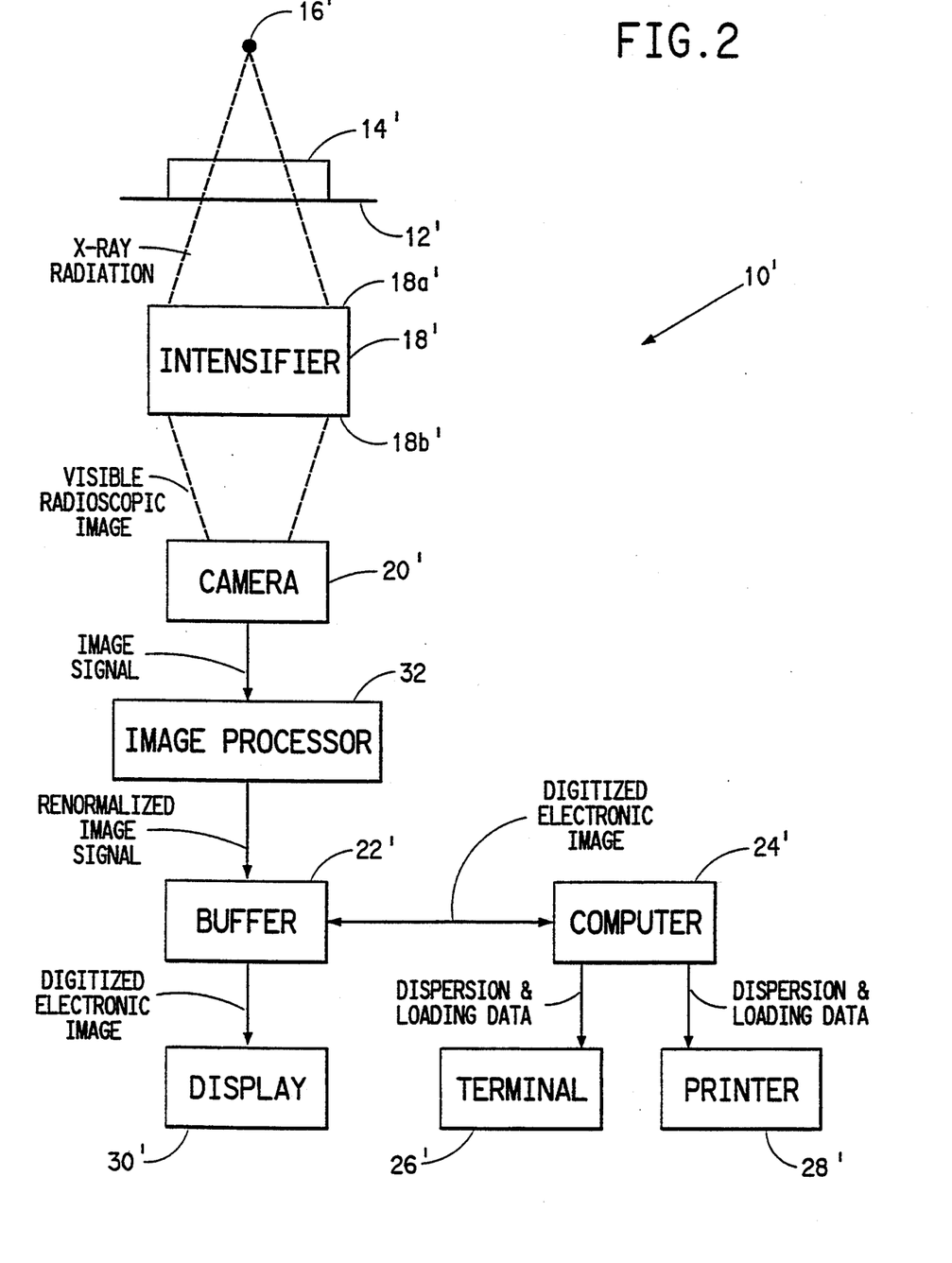
FIG. 2 is a schematic view of a second embodiment of the apparatus of the present invention.

In a second embodiment of the present invention, the apparatus for determining at least one of the dispersion and the loading of reinforcing material in a composite material further comprises an image processor connected to the image recording means for renormalizing the gains and offsets of the image signal. As shown in FIG. 2, an image processor 32 is connected to video camera 20'. Image processor 32 renormalizes the gains and offsets as discussed above of the latent image as it is transformed to an image signal. In addition, image processor 32 also averages successive video frames together to improve the signal-to-noise ratio. In all other respects, the embodiment of FIG. 2 is like the embodiment of FIG. 1, and thus components in the embodiment of FIG. 2 are designated by the same reference numeral as like components of the embodiment of FIG. 1, but are shown in FIG. 2 with a prime (').

Figure 3:
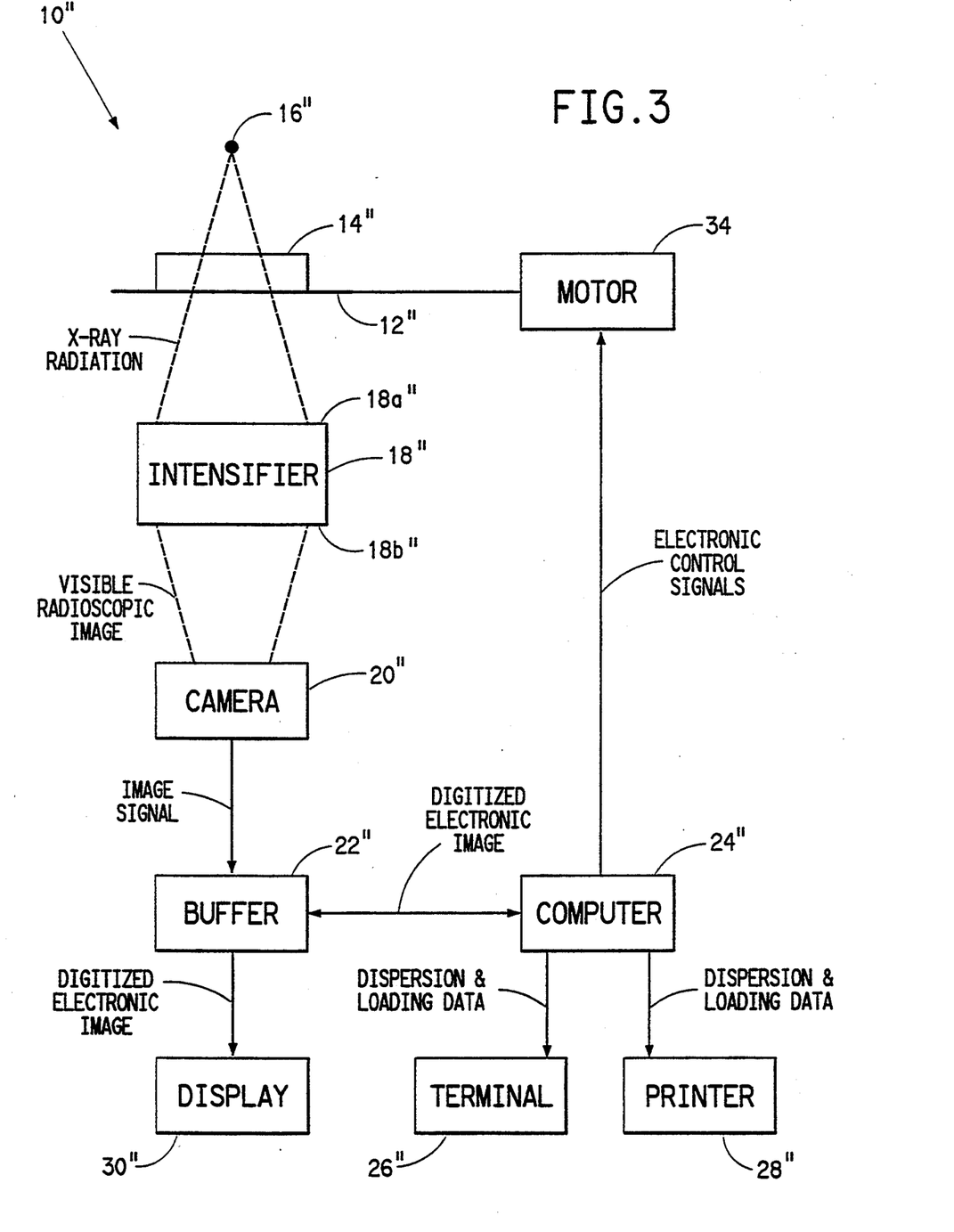
FIG. 3 is a schematic view of a preferred or third embodiment of the apparatus of the present invention.

A preferred or third embodiment of the present invention is shown in FIG. 3. Wherever possible, the components in this preferred embodiment will be designated by the same reference numeral as like components of the embodiment of FIG. 1, but will be designated with a double prime (").

Apparatus 10" includes an X-Y table 12" for holding and moving the sample into position for analysis. Table 12" is driven by driving means, which may include a stepper motor 34 which is shown in FIG. 3 mechanically linked to table 12", or any other suitable driving means, such as an asynchronous motor or a D.C. motor. Table 12" moves in a plane which is orthogonal to the axis of X-ray source 16" sample 14" and intensifier 18". Microcomputer 24" controls motor 34, so that the apparatus of the embodiment of FIG. 3 is fully automated. Thus, in the embodiment of FIG. 3, the sample comprises a batch of test bars, and microcomputer 24" consecutively analyzes each one of the test bars in the batch, providing an analysis of at least one of the dispersion and the loading for each test bar. When the dispersion and the loading are both analyzed, they are done so simultaneously. In contrast, in the embodiments of FIGS. 1 and 2, a single test bar is placed in the sample holder and the analysis is performed on one test bar at a time. In all other respects, the embodiment of FIG. 3 is like the embodiment of FIG. 1.

The operation of the automated embodiment of FIG. 3 will be explained, and the operation of the embodiments of FIGS. 1 and 2 will be readily apparent from this explanation. In operation, at least one sample 14" of composite material is held on X-Y table 12". Microcomputer 24" controls the movement of stepper motor 34, which drives X-Y table 12". X-ray source 16" passes X-ray radiation through the sample to produce a latent X-ray image of the sample. The radiation passing through the sample impinges on input screen 18a" of image intensifier 18" and output screen 18b" displays a visible radioscopic image of sample 14". Video camera 20" records the radioscopic image of the sample and generates an image signal. Buffer 22" receives the image signal generated by video camera 20" and produces a digitized electronic image from the image signal. Video display 30" displays the digitized electronic image, and microcomputer 24" analyzes the digitized electronic image to determine at least one of the dispersion and the loading of the reinforcing material in sample 14".

Figure 4:
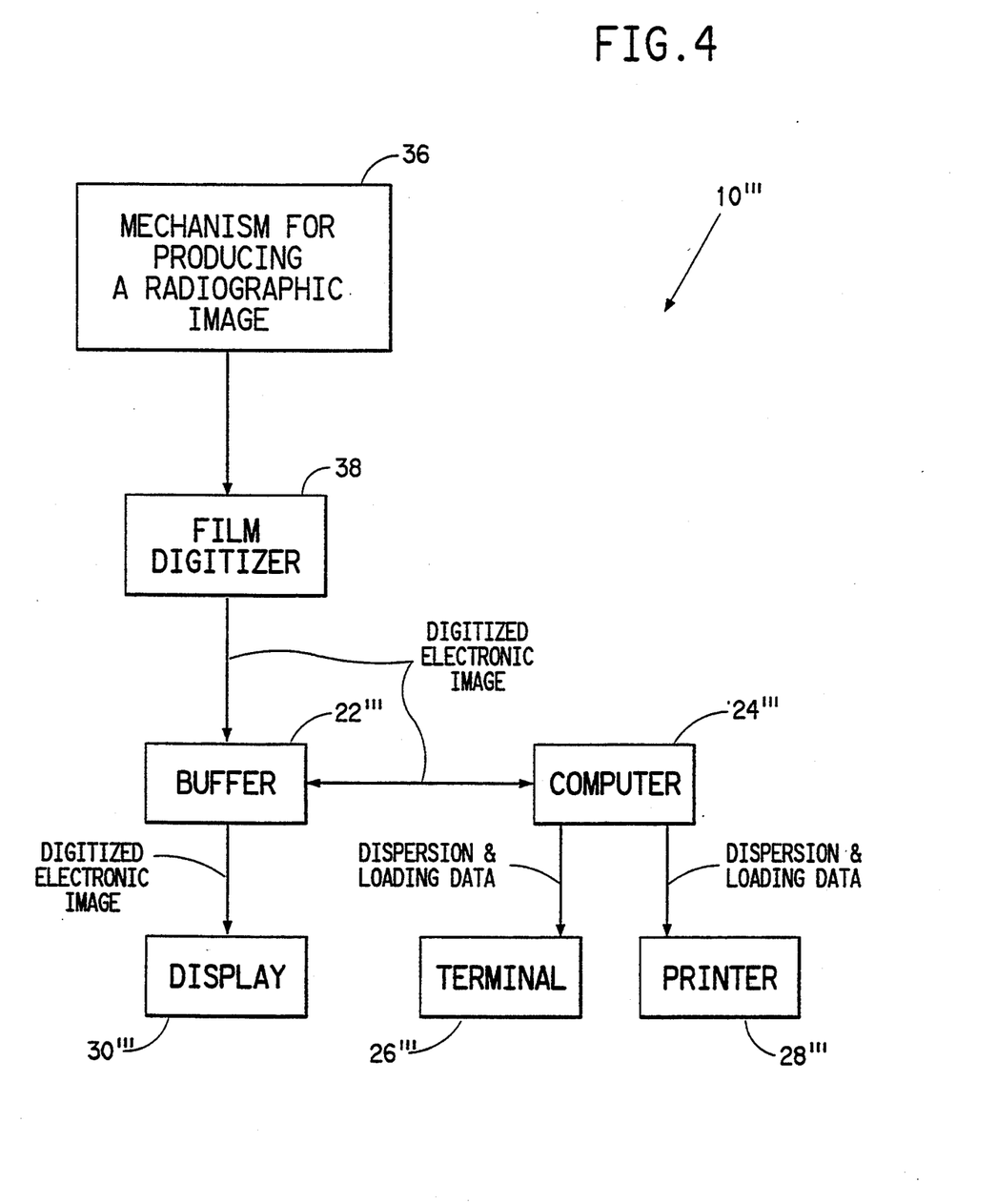
FIG. 4 is a schematic view of a fourth embodiment of the apparatus of the present invention.

An apparatus for determining at least one of the dispersion and the loading of reinforcing material in a composite material of a fourth embodiment of the present invention is shown in FIG. 4. Wherever possible, the components in the fourth embodiment will be designated by the same reference numeral as like components of the embodiment of FIG. 1, but will be designated with a triple prime ('").

The apparatus of the fourth embodiment is shown generally at 10'" in FIG. 4. Apparatus 10'" comprises means for producing a film-based radiographic image of a sample of the composite material. The means for producing a film-based radiographic image (i.e., a radiograph) are shown as box 36 in FIG. 4. Box 36 may comprise an X-ray source, the sample, radiographic film and a film processor as known in the art.

The apparatus of the fourth embodiment further comprises means for producing a digitized electronic image from the radiographic image and computer means for analyzing the digitized electronic image to determine at least one of the loading and the dispersion of the reinforcing material in the sample. The means for producing a digitized electronic image comprises a film digitizer 38 as shown in FIG. 4. Buffer 22'" receives the digitized electronic image and sends it to microcomputer 24'" or display 30'", which function in a like manner as microcomputer 24 and display 30, respectively, of the embodiment of FIG. 1.

In operation, a film-based radiographic image of a sample 14'" of the composite material is produced by radiographic image producing means 36. A digitized electronic image is then produced by film digitzer 38. The gains and losses of the digitized electronic image are renormalized by microcomputer 24'". The renormalized, digitized electronic image is then analyzed by microcomputer 24'" to determine at least one of the loading and the dispersion of the reinforcing material in the sample as explained below.

In all of the embodiments of the present invention, the digitized electronic image is analyzed according to the following principles. Due to noise in the image intensifier, it is preferable to average several images together in buffer 22, 22' and 22". It may also be necessary to renormalize the digitized electronic image with microcomputer 24, 24" and 24'" as in the embodiment of FIGS. 1, 3 and 4, or to renormalize the image signal with image processor 32 as in the embodiment of FIG. 2. Once the digitized electronic image or the image signal has been renormalized, in order to determine dispersion in a region of interest of the image, the pixels that comprise the image are analyzed to determine the average and standard deviation of the gray levels of the renormalized, digitized electronic image. For a sample with substantially uniform thickness, the more evenly distributed the reinforcing material is, the more uniformly gray will be the resultant renormalized, digitized electronic image. Consequently, the standard deviation of the gray level values will be small for samples with uniform fiber dispersion.

Loading can be determined from the average gray level of the pixels of the region of interest. The computer uses the following equations to determine loading:

$$\mu = -ln(I/I_0)/t \tag{1}$$

$$\alpha = (\mu_s - \mu_n)/(\mu_g - \mu_n) \tag{2}$$

$$\beta = \alpha/[\alpha(1-R)+R] \tag{3}$$

where:
$\alpha$ = volume loading (glass fraction by volume)
$\beta$ = weight loading (glass fraction by weight)
t = sample thickness
$\mu_s$ = calculated linear attenuation coefficient of the sample measured in inverse centimeters [1/cm]
$\mu_g$ = linear attenuation coefficient of reinforcing material measured in inverse centimeters [1/cm]
$\mu_n$ = linear attenuation coefficient of matrix measured in inverse centimeters [1/cm]
R = density ratio ($\rho$ of composite material)/$\rho$ of reinforcing material)
I = average gray level value; and
$I_0$ = reference level (gray level with no sample)

Equivalently, these equations can be applied to each of the individual gray level values to determine the loading at each pixel. The average of the loading values can be taken to determine the loading of the sample. In practice, it has been found that this loading is equivalent to the loading calculated by taking the average gray level value of all the pixels and applying the above equations to the average gray level value to determine loading.

Figure 5A:
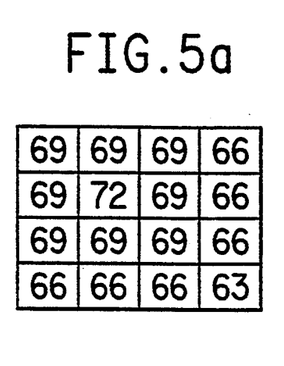
FIGS. 5a–5d are exemplary 4×4 arrays that illustrate the method used to determine spatial variations in the reinforcing material content of a hypothetical sample.

It has been found useful to provide a map showing variations in the amount of reinforcing material across the surface of a sample. This mapping method is equally applicable to all the embodiments of the present invention. The method of mapping the variation in the amount of reinforcing material in a composite material comprises the steps of producing a through-transmission projection image of a sample of the composite material and generating an image signal from the through-transmission projection image; these steps are achieved as discussed in the embodiments of FIGS. 1-3 above. Alternatively, the method comprises the steps of producing a radiographic image of a sample of the composite material and generating an image signal of the radiographic image; these steps are achieved as discussed in the embodiment of FIG. 4 above. The method further comprises the steps of producing a digitized electronic image of the image signal, renormalizing the gains and offsets in the digitized electronic image and determining the local gray level values of the renormalized, digitized electronic image at a predetermined resolution, for either a radioscopic or a radiographic image. Alternatively, the image signal may be renormalized with an image processor as in the embodiment of FIG. 2, the renormalized image signal may be used to produce a digitized electronic image, and the local gray level values of the digitized electronic image at a predetermined resolution may then be determined. As discussed above, each value of gray level corresponds to a specific level of loading. As an example of this process, FIG. 5a shows a hypothetical 4×4 renormalized, digitized electronic image. There are a total of 16 pixels in this image, and it is assumed that 100% transmission of the incident radiation ($I_0$) corresponds to a gray level value of 100.

Figure 5B:
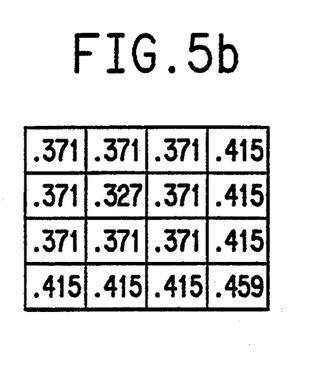

The method of mapping the variation in the amount of reinforcing material in a matrix of composite material further comprises the step of calculating the local attenuation coefficients of the sample from each of the gray level values. Applying equation (1) above to the data in FIG. 5a yields another 4×4 array of values for $\mu_s$, the attenuation coefficient of the sample. This array is shown in FIG. 5b. This analysis assumes that the total thickness of the sample is known. As long as the sample thickness can be measured or estimated (via the geometry of the sample), the attenuation coefficient can be determined.

Figure 5C:
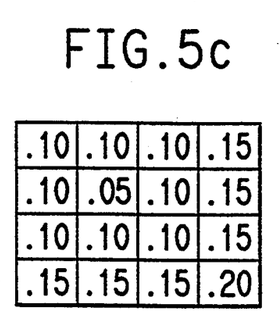
Figure 5D:
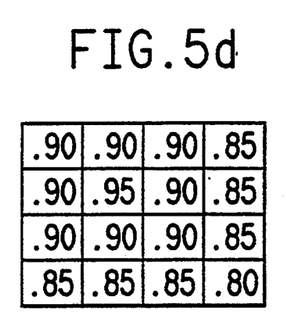

The method of mapping the variation in the amount of reinforcing material in a composite material further comprises the step of determining the local loading values from each of the local attenuation coefficients. Equation (2) above relates the array of $\mu_s$ values to a 4×4 array of values for $\alpha$, the reinforcing material volume fraction of the sample which is shown in FIG. 5c. The fractional number of FIG. 5c represents the fraction of reinforcing material. If the matrix content is required, then it is necessary only to recognize that for a fully consolidated sample, reinforcing material content plus resin content equals 100%, so the 4×4 array of FIG. 5c can be subtracted from 1.0 to obtain a final array of the matrix volume fraction. This array is shown in FIG. 5d. This array can be displayed as an image showing the content of the reinforcing material and the matrix of the composite material. Of course, the foregoing is only an example. In practice, it is possible to have much higher resolution images (e.g., a 512×512 matrix) having a correspondingly greater number of pixels. It should be noted that the pixels in the sub-regions in a high-resolution map may be averaged to produce local loadings in a low-resolution map on TV display 30, 30', 30" and 30"'.

The method of mapping the variation in the amount of reinforcing material in a composite material further comprises the step of averaging the local loading values to determine an average loading value of the sample. The local loading values as shown in FIG. 5d may be averaged to determine an average loading value of the sample.

The analysis used above assumes that the material system has only two phases, i.e., a matrix phase and a reinforcing material phase. It also assumes that the attenuation coefficients of the component materials are known or can be measured. In a two-phase system consisting of a matrix A reinforced with a material B, there is only one unknown quantity—the volume fraction of B. Equation (2) above defining $\alpha$, the volume fraction, relates this single unknown quantity to a single measurable quantity—the attenuation coefficient of the sample, $\mu_s$.

In a more complicated case, where a three-phase sample consists of a matrix A reinforced with materials B and C, two independent equations are needed to determine the two unknown quantities, the volume fraction of B and the volume fraction of C. In principle, it is possible to obtain a second independent equation by considering the attenuation of radiation in a different energy regime. The attenuation coefficient is a function of wavelength (i.e., radiation energy) and material composition. In general, the energy dependence of the attenuation coefficient is different for any two materials, so the coefficients will be linearly independent at two different energies. If attenuation measurements of a composite three-phase sample are made at two separate and distinct X-ray energies, there are two linearly independent equations and only one unknown quantity, so the volume fractions of both B and C can be determined. In general, for a composite with N phases, this same technique in principle could be used to determine loading as long as attenuation measurements were made at $N-1$ distinct energies; the attenuation coefficients would need to be known at each of these energies for each of the component phases. It may be possible to determine volume fractions in a multiphase material system using measurements at a single X-ray energy under certain circumstances, as described in Example 4 below.

The invention will be further clarified by the following examples, which are intended to be purely exemplary of the invention.

EXAMPLE 1

Two test bars of glass fiber-reinforced nylon 66 were prepared to illustrate the features of the present invention. Test bar 1A, exhibiting poor glass fiber dispersion, was specifically prepared so that the test bar contained conglomerates of reinforcing material within the resin matrix. A test bar 1B exhibiting good glass fiber dispersion was prepared, ensuring that the reinforcing material was as uniformly dispersed throughout the matrix as possible.

Test bar 1A was prepared by dry-blending approximately 1300 g of glass fibers (type OCF-127AAA, ⅛" long, commercially available from Owens-Corning Fiberglass Corp., located in Granville, Ohio) with approximately 1700 g of pellets of nylon 66 (commercially available from E.I. du Pont de Nemours and Company, (Inc.) of Wilmington, Del., hereinafter referred to as "Du Pont", sold under the trademark "Zytel", hereinafter referred to as "ZYTEL") ZYTEL ST801 pellets. The mixture was subsequently dried in a vacuum oven for approximately 20 hours at 90 degrees Celsius. After drying, the mixture was fed directly to an injection molding machine to produce a test bar having the approximate dimensions 4.5"×0.5"×0.125".

Test bar 1B was prepared from commercially available pellets of glass fiber-reinforced nylon 66, (ZYTEL 70G33, 33 wt % glass, commercially available from Du Pont). In the manufacture of these pellets, the glass fibers are extruded with the nylon, so that the fibers are well-dispersed. The pellets were fed into an injection molding machine to produce a test bar of the same size and shape as test bar 1A.

Test bars 1A and 1B were analyzed for dispersion by producing renormalized, digitized electronic images as discussed above and selecting that portion of the image corresponding to the test bar (designated as the region of interest). In order to provide the data necessary for renormalization, a digitized electronic image ("black level") was obtained by averaging 100 video frames of the camera output with a lead shutter between the X-ray source and the image intensifier. Next the "white level" was obtained by averaging 100 video frames from the camera with the X-ray source (operating at a plate voltage of 42 keV with a beam current of 87 μA) directly illuminating the intensifier. The renormalized, digitized electronic image was produced by averaging 100 video frames from the camera and applying the renormalization formula on a pixel-by-pixel basis:

$$output(x,y) = 200*[input(x,y) - black(x,y)]/white(x,y)$$

where:
(x,y) = specific pixel location in the image
input = average of 100 video frames
output = renormalized electronic image
black = "black level" data measured above
white = "white level" data measured above; and
The factor of 200 is an arbitrary scale factor introduced during renormalization. It is removed before calculating the attenuation coefficient of the test bar.

Figure 6:
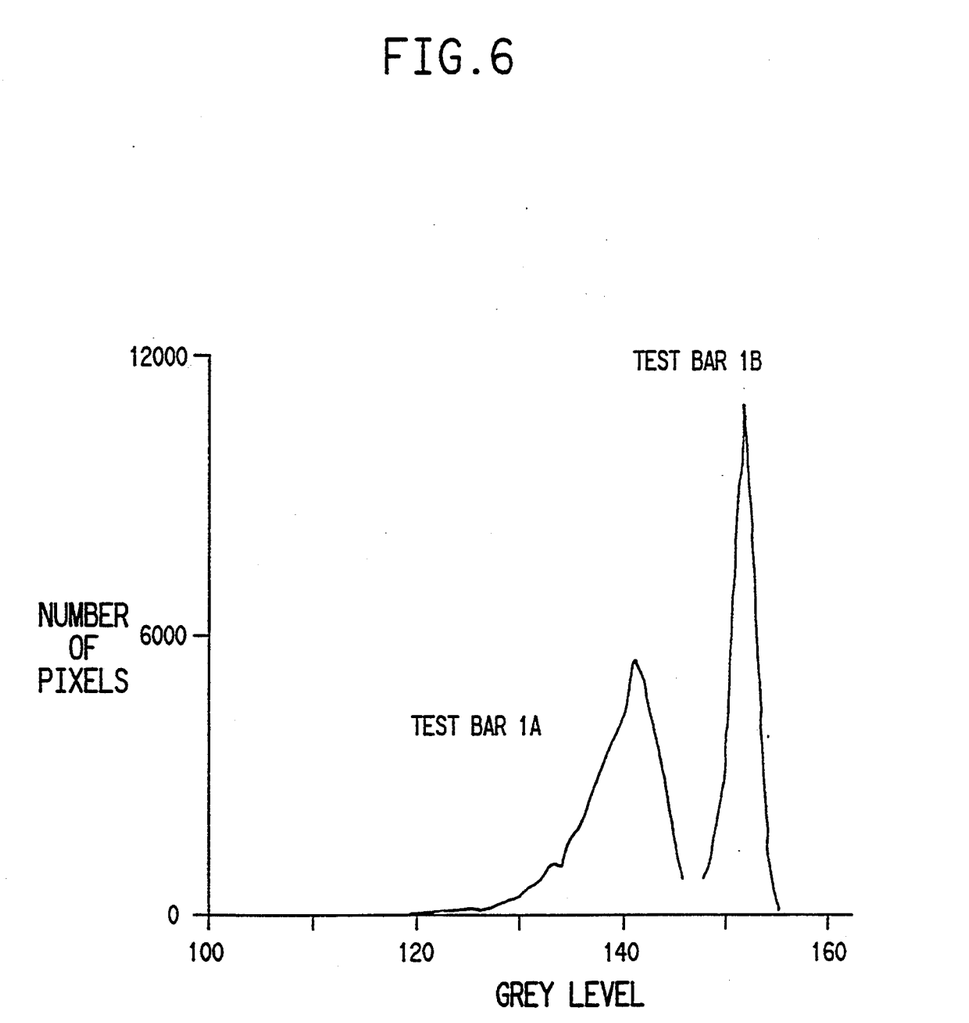
FIG. 6 is a histogram showing the distribution of gray levels in a radioscopic image for both a test bar with good fiber dispersion and a test bar with poor fiber dispersion analyzed with the apparatus of the preferred embodiment of the present invention and described in Example 1.

The histogram of the gray level values of the pixels in the region of interest was generated and plotted for each of the two test bars. As shown in FIG. 6, the distribution of gray levels in the renormalized, digitized electronic image is directly correlated with the quality of dispersion of reinforcing material in the test bars, where a narrow distribution is an indication of good dispersion, as exhibited by test bar 1B.

A numerical value for the width of the distribution of gray level values can be expressed as the standard deviation of those values. For example, the standard deviation of test bar 1A is about 5.5, and the standard deviation of test bar 1B is about 1.5. Thus, the standard deviation of the gray level values in the region of interest of the renormalized, digitized electronic image can be used as a quantitative, objective measurement of the quality of dispersion of reinforcing material.

Referring again to FIG. 6, it is apparent that the centroid of the gray level distribution is not the same for both test bars. The average gray level is lower for test bar 1A than it is for test bar 1B. This is due to the fact that there is a greater amount of glass present in test bar 1A.

By applying the method described above, it is possible to determine the glass fiber loading from the average gray level value in the region of interest. An example of this measurement is given in Example 2 below.

EXAMPLE 2

Seven lots 2A-2G of five test bars each were molded from various compositions of glass and nylon 66 (ZYTEL ST801) as summarized in Table 1 below.

TABLE 1

| Lot | Compounding Method* | Wt % | Glass Type** |
|-----|---------------------|------|--------------|
| 2A  | A                   | 50%  | 473-CB-675   |
| 2B  | B                   | 40%  | 497          |
| 2C  | C                   | 40%  | 497          |
| 2D  | B                   | 40%  | 473          |
| 2E  | C                   | 40%  | 473          |
| 2F  | C                   | 50%  | 473-CB-675   |
| 2G  | C                   | 50%  | 473-CB-675#  |

*Compounding Methods:
A: Glass and nylon pellets were dry-blended and injection molded using a first type of mixing screw.
B: Glass and nylon pellets were mixed in a twin-screw extruder and injection molded with a second type of mixing screw.
C: Glass and nylon pellets were dry-blended and injection molded using the second type of mixing screw.
**Fiberglass available in ¼" lengths from Owens-Corning Fiberglass Corp.
A different sizing was used on the fiberglass.

Using the computer to make the above measurements automatically, each half of each 4.5"×0.5"×0.125" test bar was examined for a total of 10 measurements per lot, giving a total of 70 measurements. In order to provide the data necessary for renormalization, the "black" level and the "white level" were obtained as in Example 1. Next, the measurements were made as follows: Up to 25 of the 35 bars were placed on the X-Y table at a time. After the test bars were placed on the X-Y table and the X-ray source was energized to 42 keV at 87 μA of beam current, the automatic analysis program was started. The X-Y table, which was driven by a motor controlled by the computer, was moved to position the next test bar between the X-ray source and the image intensifier, and a renormalized, digitized electronic image was calculated by averaging 100 video frames from the camera and applying the renormalizing formula as in Example 1.

Figure 7:
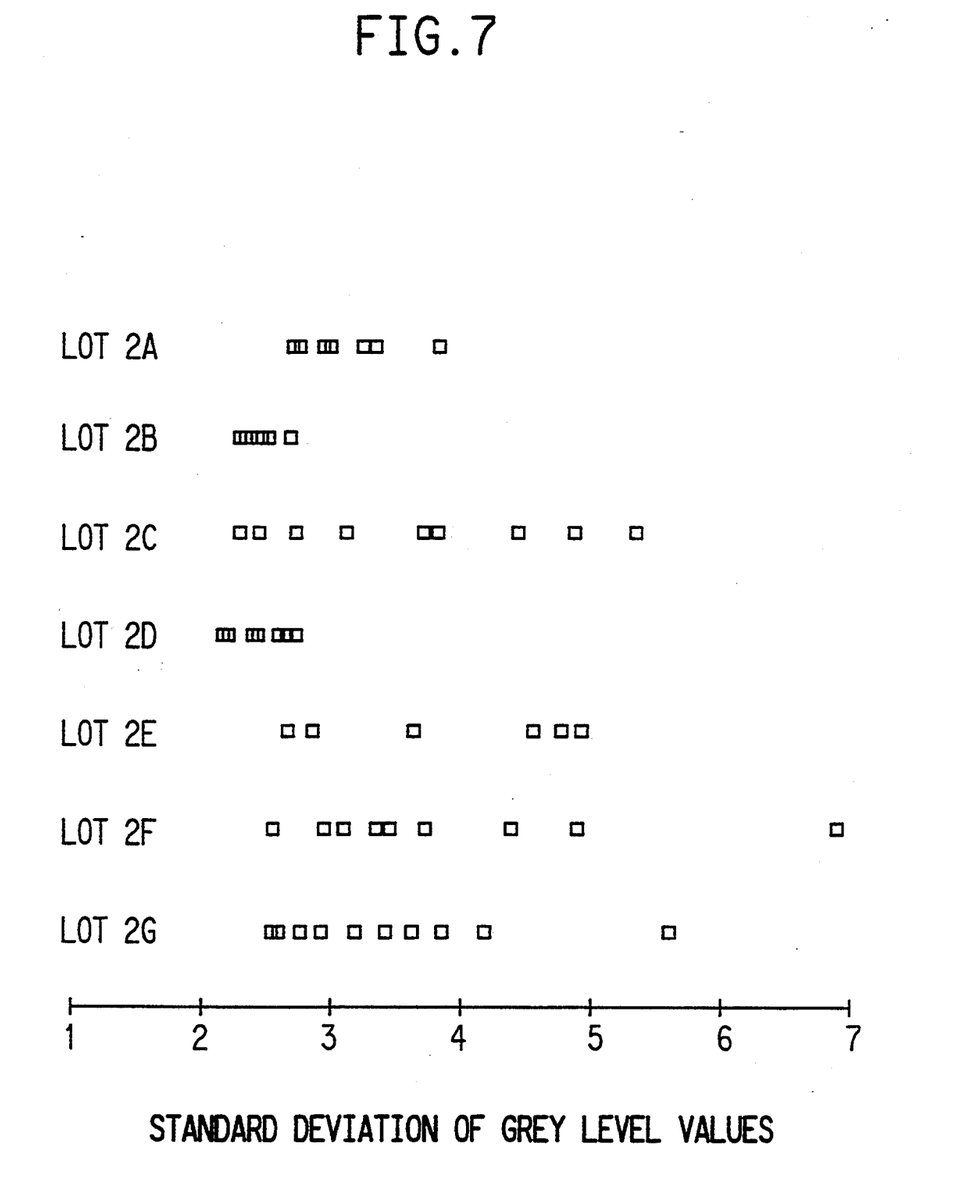
FIG. 7 is a graph showing the standard deviation of the gray level values for test bars analyzed with the apparatus of the preferred embodiment of the present invention and described in Example 2.

The standard deviation of the gray level values of each pixel in the region of interest was then computed for each of the 70 measurements. The results, shown in FIG. 7, indicate that the glass fibers dispersed well in some lots but not in others. These results correlated well with a qualitative visual inspection of the test bars. It should be noted that the test bars exhibiting poor glass dispersion may give a wide range of standard deviations, depending on where the region of interest is located on the bar. This effect is due to the scale of the dispersion being on the order of the size of the chosen region of interest. By measuring several bars (or one larger test bar) it is possible to determine a global value for the dispersion in a particular material system. In some cases where the dispersion is fairly uniform, a single measurement is sufficient to characterize the dispersion in that material system.

After determining the standard deviation from the region of interest in the renormalized, digitized electronic image, the average gray level value in the region of interest was used to determine the glass loading (volume fraction) in the bar. The following equations were used to determine the loading for each of the 70 measurements:

$$\mu = -\ln(avg/200)/t \qquad (1)$$

$$\alpha = (\eta_s - \mu_n)/(\mu_g - \mu_n) \qquad (2)$$

$$\beta = \alpha/[\alpha(1-R)+R] \qquad (3)$$

where:
  $\alpha$ = volume loading (glass fraction by volume)
  $\beta$ = weight loading (glass fraction by weight)
  t = test bar thickness = 0.317 cm
  $\mu_s$ = calculated attenuation coefficient of the test bar, [1/cm]
  $\mu_g$ = attenuation coefficient of glass = 3.5 1/cm @ 42 keV
  $\mu_n$ = attenuation coefficient of nylon = 0.30 1/cm @ 42 keV
  R = density ratio ($\rho$ of nylon)/($\rho$ of glass)
  $\rho$ = of nylon = 1.08 g/cc p2 $\rho$ = of glass = 2.55 g/cc
  avg = average pixel gray level values in the region of interest; and The factor of 200 is an arbitrary scale factor introduced during renormalization. It is removed from the data before calculating the attenuation coefficient of the test bar.

The values for $\mu_g$ and $\mu_n$ were determined empirically beforehand by measuring the average gray level for both a test bar of glass and a test bar of glass-free nylon 66 (ZYTEL ST801) and applying the equation $\mu = -\ln(\text{avg}/200)/t$.

Figure 8:
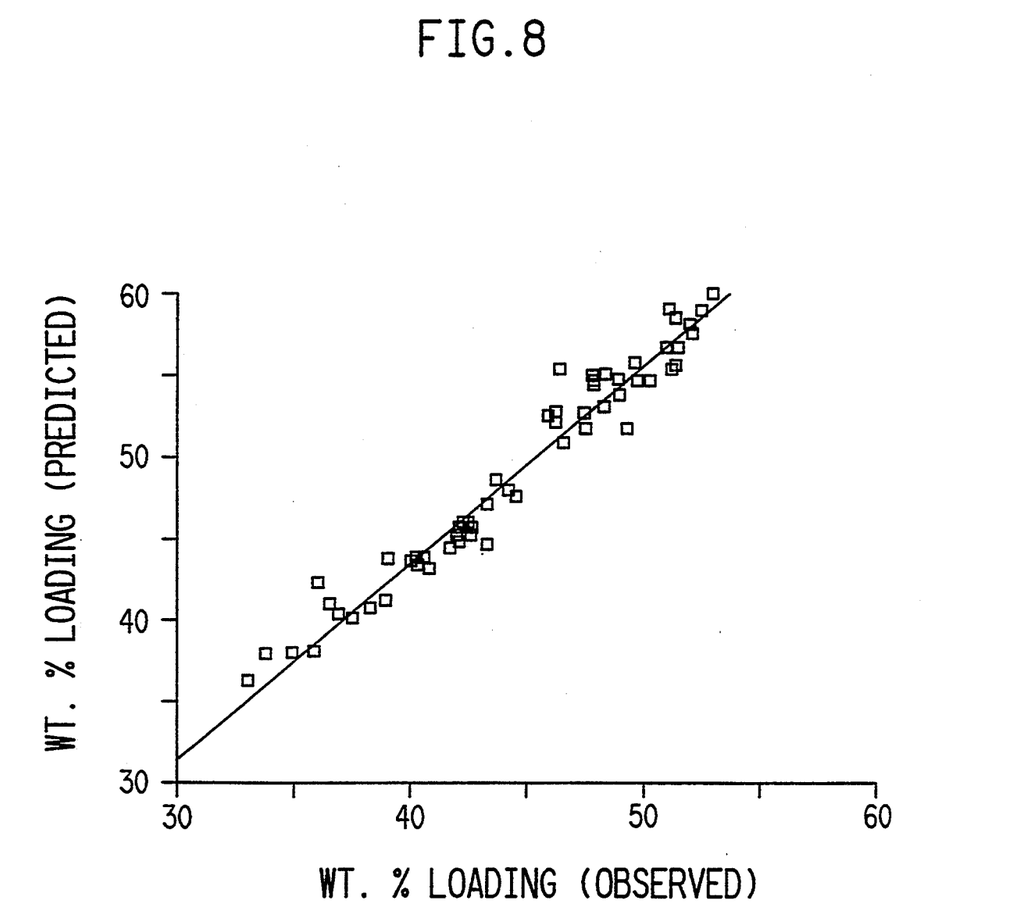
FIG. 8 is a graph showing the correlation of percent loading predicted by the prior art method of ashing and the percent loading observed using the apparatus of the preferred embodiment of the present invention and described in Example 2.

The standard deviation and loading measurements were then tabulated in a standard format. After these nondestructive measurements were completed, the bars were cut in half, weighed and ashed using prior art ashing methods. By washing the ash from the residue, weighing the residual glass and taking the ratio of glass weight to the initial weight of the bars, the glass loading of these test bars was determined. The results of the nondestructive loading measurements are compared to the ashing measurements in FIG. 8. The correlation between the two sets of measurements is very good (the coefficient of correlation is 0.987).

EXAMPLE 3

As an example of a different material system, five test bars were made of graphite fibers (type AS4-G-3K, available from Hercules, Inc. of Wilmington, Delaware) dispersed in a matrix of polytetrafluoroethylene, (sold under the trademark "Teflon" and hereinafter referred to as "TEFLON") or TEFLON PFA 340, commercially available from Du Pont. The test bars were molded as in the above examples. Carbon fibers were first weighed, then melt-coated with TEFLON PFA 340; the coated fibers were weighed and determined to be about 70 wt % TEFLON PFA 340. Then, 1.7 pounds of coated carbon fibers (1.2 pounds of TEFLON PFA 340, 0.5 pounds of carbon fiber) were mixed with 1.4 pounds of TEFLON PFA 340 pellets and injection molded into test bars 3A–3E. Based on the amount of material fed into the injection molding machine, the test bars were expected to contain about 16 wt % carbon. These test bars were placed into the apparatus of the present invention and analyzed using the automatic system as in Example 2. A report was automatically printed by the computer after all measurements were completed. Table 2 below shows the results of those measurements; the designation N or F refers to the two measurement locations on each test bar.

TABLE 2

| Sample | Mean | Standard Deviation | Vol. % | Wt. % |
| --- | --- | --- | --- | --- |
| 3A-N | 157.45 | 0.98 | 10.8% | 9.2% |
| 3A-F | 158.66 | 0.83 | 17.5% | 15.0% |

TABLE 2-continued

| Sample | Mean | Standard Deviation | Vol. % | Wt. % |
| --- | --- | --- | --- | --- |
| 3B-N | 157.23 | 1.00 | 9.6% | 8.2% |
| 3B-F | 158.52 | 0.84 | 16.7% | 14.3% |
| 3C-N | 157.67 | 0.87 | 12.0% | 10.2% |
| 3C-F | 158.62 | 0.88 | 17.2% | 14.8% |
| 3D-N | 157.35 | 0.88 | 10.2% | 8.7% |
| 3D-F | 158.27 | 0.88 | 15.3% | 13.1% |
| 3E-N | 157.33 | 0.85 | 10.1% | 8.6% |
| 3E-F | 158.04 | 3.10 | 13.8% | 11.8% |

The density and attenuation values for carbon and TEFLON PFA 340 of the above table have been substituted for those of glass and ZYTEL ST801 in order to compute the loading correctly. The carbon loading as measured according to the method of the present invention was found to range from 9 to 15 wt %, which is close to the expected value of 16 wt %. It is noted that there is no known technique other than the method of the present invention that could be used as an independent measure of the carbon loading in these test bars.

EXAMPLE 4

Four test bars 4A–4D were injection molded as in the above examples. Test bar 4A was molded from a mixture 4-MIX-1 of fiberglass (OCF-127-AAA) and TEFLON PFA 340; test bar 4B was molded from a mixture 4-MIX-2 of carbon fiber (AS4-G-3K) and TEFLON PFA 340 as in Example 3; test bar 4C was molded from a mixture (4-MIX-3) of 4-MIX-1 and 4-MIX-2; and test bar 4D was molded from a different mixture (4-MIX-4) of 4-MIX-1 and 4-MIX-2. Thus, test bars 4C and 4D both contained carbon and glass fibers in a matrix of TEFLON PFA 340. A renormalized, digitized electronic image was produced for each of the four test bars 4A–4D. The average gray level was determined for each test bar as in Example 2 above. The attenuation coefficients were calculated using $\mu = -\ln(\text{avg}/200)/t$. The observed values were:

TABLE 3

| Test bar | Observed Value (1/cm) |
| --- | --- |
| 4A: | 1.22 |
| 4B: | 0.71 |
| 4C: | 1.14 |
| 4D: | 1.01 |

Applying loading equation (2) shown above in Example 2 to this data, it was determined that 4-MIX-1 was 14.8 vol % glass (the balance was TEFLON), 4-MIX-2 was 5.5 vol % carbon (the balance was TEFLON). Using the attenuation coefficients for test bars 4A and 4B in lieu of the attenuation of TEFLON PFA 340 and carbon (or glass), it was also possible to determine that 4C was 84.5 vol % 4-MIX-1 (and 15.5% vol % 4-MIX-2) and that 4D was 59.2 vol.% 4-MIX-1 (and 40.8 vol. 4-MIX-2). Since it was known that 4-MIX-3 and 4-MIX-4 were binary mixtures of 4-MIX-1 and 4-MIX-2, the composition of the three-phase test bars 4C and 4D could be determined as follows:

TABLE 4

| Test bar | vol % glass | vol % TEFLON | vol % carbon |
| --- | --- | --- | --- |
| 4C | 12.5 | 82.0 | 5.5 |
| 4D | 8.8 | 76.8 | 14.5 |

This example demonstrates how the composition of a multiphase sample may be determined using measurements at a single X-ray energy. However, in the general case where intermediate binary mixtures (such as 4-MIX-1 and 4-MIX-2 in the present example) are not available, measurements must be made at a multiple of X-ray energies as discussed above.

Additional advantages and modifications will readily occur to those skilled in the art. The invention in its broader aspects is, therefore, not limited to the specific details, representative apparatus and illustrative examples shown and described. Accordingly, departures may be made from such details without departing from the spirit or scope of the general inventive concept as defined by the appended claims and their equivalents.

I claim:

1. An apparatus for determining the mechanical strength of a composite material, the composite material including a reinforcing material and a matrix, the composite material having an average linear attenuation coefficient and the reinforcing material and the matrix each having a linear attenuation coefficient, comprising:
   (a) means for producing a visible, radioscopic image of a sample of the composite material including a sample holder for holding the sample;
   (b) image recording means for recording the radioscopic image of the sample and for generating an image signal from the radioscopic image;
   (c) buffer means for receiving the image signal and for producing a digitized electronic image from the image signal; and
   (d) computer means for analyzing the digitized electronic image to determine the average linear attenuation coefficient of the composite material, for calculating the volume fraction loading of the reinforcing material in the composite material from the linear attenuation coefficients of the reinforcing material and the matrix, respectively, and the average linear attenuation coefficient of the composite material, and for comparing the calculated volume fraction loading to a predetermined value in order to determine the mechanical strength of the composite material.

2. The apparatus of claim 1, wherein the digitized electronic image has gains and offsets and the computer means renormalizes the gains and offsets of the digitized electronic image.

3. The apparatus of claim 1, further including an image processor connected to the image recording means, wherein the image signal has gains and offsets and the image processor renormalizes the gains and offsets of the image signal.

4. The apparatus of claim 1, further including image display means connected to the buffer means for displaying the digitized electronic image.

5. The apparatus of claim 1, wherein the sample roller comprises an X-Y table.

6. The apparatus of claim 5, further including driving means for moving the X-Y table, wherein the computer means controls the driving means.

7. The apparatus of claim 1, wherein the sample comprises one of a test bar and a manufactured part.

8. The apparatus of claim 1, wherein the sample comprises a batch of test bars and further wherein the computer means analyzes at least one of the dispersion and the loading for each of the test bars in the batch.

9. An apparatus for determining the quality of dispersion of a reinforcing material in a composite material, comprising:
   (a) an image intensifier for producing a through-transmission projection image of a sample of the composite material;
   (b) means for producing a digitized electronic image from the through-transmission projection image; and
   (c) computer means for calculating the standard deviation of the gray level values in the digitized electronic image and for comparing the calculated standard deviation to a predetermined value in order to determine the quality of dispersion of the reinforcing material in the composite material.

10. An apparatus for determining both the quality of dispersion and the mechanical strength of a composite material, the composite material including a reinforcing material and a matrix, the composite material having an average linear attenuation coefficient and the reinforcing material and the matrix each having a linear attenuation coefficient, the apparatus comprising:
   (a) an X-ray source for producing a through-transmission projection image of a sample of the composite material;
   (b) means for producing a digitized electronic image from the through-transmission projection image; and
   (c) computer means for calculating the average linear attenuation coefficient of the composite material from the digitized electronic image, for calculating the volume fraction loading of the reinforcing material in the composite material from the average linear attenuation coefficient of the composite material, and the linear attenuation coefficients of the reinforcing material and the matrix, respectively, for comparing the calculated values for the volume fraction loading to a predetermined value in order to determine the mechanical strength of the composite material, for calculating the standard deviation of the gray level values in the digitized electronic image and for comparing the calculated standard deviation to a predetermined value in order to determine the quality of dispersion of the reinforcing material in the composite material.

* * * * *